United States Patent
Matlock

(10) Patent No.: US 6,270,432 B1
(45) Date of Patent: Aug. 7, 2001

(54) TENNIS TRAINING AND DRILLING DEVICE

(76) Inventor: Linda T. Matlock, 2673 NY Rte. 43, Averill Park, NY (US) 12018

(*) Notice: Subject to any disclaimer, the term of this patent is extended or adjusted under 35 U.S.C. 154(b) by 0 days.

(21) Appl. No.: 09/394,603

(22) Filed: Sep. 13, 1999

(51) Int. Cl.$^7$ .................................................. A63B 69/00
(52) U.S. Cl. ...................... 473/464; 473/217; 482/900; 340/323 R; 340/666; 340/573.1; 36/136; 36/139
(58) Field of Search ................... 473/218, 270–271, 473/458–459, 425, 452, 464, FOR 115, FOR 106; 36/132, 136, 137; 482/900, 901, 902; 434/247, 252; 340/323 R, 574, 328, 666, 689, 573.1, 546, 276; 273/DIG. 18; 439/37

(56) References Cited

U.S. PATENT DOCUMENTS

| | | | |
|---|---|---|---|
| 3,432,964 | * 3/1969 | Visitacion | 36/139 |
| 3,702,999 | * 11/1972 | Grandisar | 340/573.1 |
| 3,777,086 | * 12/1973 | Riedo | 200/52 R |
| 3,878,641 | * 4/1975 | Nobel | 273/DIG. 18 |
| 4,660,829 | 4/1987 | Whitneir . | |
| 4,667,188 | * 5/1987 | Schwartz | 340/689 |
| 4,956,628 | * 9/1990 | Furlong | 340/323 R |
| 5,005,002 | * 4/1991 | Halperin | 340/574 |
| 5,051,095 | * 9/1991 | Slenker | 439/37 |
| 5,221,088 | 6/1993 | McTeigue et al. . | |
| 5,253,654 | * 10/1993 | Thomas et al. | 439/666 |
| 5,357,696 | * 10/1994 | Gray et al. | 36/136 |
| 5,437,289 | 8/1995 | Liverance et al. . | |
| 5,452,269 | * 9/1995 | Cherdak | 36/132 |
| 5,471,405 | 11/1995 | Marsh . | |
| 5,530,626 | * 6/1996 | Norment | 36/136 |
| 5,619,186 | * 4/1997 | Schmidt et al. | 340/573.1 |
| 5,967,171 | * 6/1998 | Dwyer, Jr. | 137/78.1 |
| 6,001,023 | * 12/1999 | Sanchez et al. | 473/217 |

* cited by examiner

Primary Examiner—Jeanette Chapman
Assistant Examiner—Mitra Aryanpour
(74) Attorney, Agent, or Firm—Heslin & Rothenberg, P.C.

(57) ABSTRACT

A sports footwork training device that immediately alerts players if their weight is not on the balls of the feet includes a switch removably attachable to a rearward portion of a lower surface of a sole of a shoe. The switch is closable by application of pressure to a heel of the shoe. An alarm, electrically coupled to the switch, is triggered when the switch is closed. A method for training a sports participant to maintain weight on a forward part of a foot is also described.

17 Claims, 2 Drawing Sheets

TENNIS TRAINING AND DRILLING DEVICE

FIELD OF THE INVENTION

The invention relates to the sport of tennis. More particularly, the invention relates to devices and methods for training and drilling tennis players to stand and move with their weight on the balls of their feet.

BACKGROUND OF THE INVENTION

It is frequently advantageous when playing tennis to play at a position close to the net. When done properly, net play can result in winning the match, because in this position, players can hit shots to the opponents' feet, placing them at a disadvantage. The opponents often miss the shot immediately, or commit an error. Net players have an additional advantage because they are hitting the ball in a downward direction, increasing the power and speed of the return, to opponents who must hit the ball in an, upward direction, resulting in a return of less power and speed.

However, it is difficult to play the net position properly, especially for beginning players. The pace of play at the net is faster than play from the baseline. Net play calls for anticipation, fast response and quick movement.

One technique that works to reduce reaction time and increase speed and, therefore, to improve play at the net, is for players to stand and move with their weight on the forward part or balls of their feet. Such a stance enables the player to respond quickly in any direction, and is a significant component in playing the net position successfully.

It can be difficult for a novice to learn to play at the net, and for instructors to teach this skill. Many simultaneous events and conditions demand attention at any particular time, making it difficult to isolate and drill many skills used in the sport of tennis. This is particularly true when learning to play at the net. Because a stance with the weight on the balls of the feet is so important to playing at the net, and because it is difficult to learn and teach this skill, there is a need for a way to unambiguously evaluate and improve footwork at the net. A device that would warn or inform players immediately when they do not have their weight on the balls of their feet would be particularly valuable. In addition, there is a need for a device for training players to use the proper stance and drilling them in the use of that stance that is effective, and relatively simple, inexpensive, convenient and easy to use.

SUMMARY OF THE INVENTION

In one aspect, the present invention relates to a sports footwork training device that immediately and effectively alerts players if their weight is not on the balls of the feet, but on the heels. A sports footwork training device according to the present invention may comprise a switch removably attachable to a rearward portion of a lower surface of a sole of a shoe, the switch closable by application of pressure to a heel of the shoe, and an alarm, electrically coupled to the switch, triggered when the switch is closed. The alarm may be an audible alarm. The switch and the alarm may be enclosed in a casing; the casing may be flexible and/or expandable. The casing may additionally comprise a battery holder. The device may additionally comprise at least one clip for removably attaching the switch to the shoe. The alarm may also be removably attachable to the shoe, by at least one clip.

In another aspect, a sports footwork training device according to the present invention comprises a switch removably attachable to a rearward portion of a lower surface of a sole of a shoe, the switch closable by application of pressure to a heel of a shoe, and an alarm, electrically coupled to the switch, triggered when the switch is open. The alarm may be removably attachable to the shoe.

In yet another aspect, a method for training a sports participant to maintain weight on a forward part of a foot, according to the present invention, comprises removably attaching, to a rearward portion of a lower surface of at least one sole of the sports participant's shoe, a switch closable by application of pressure to a heel of the shoe, and triggering an alarm, electrically coupled to the switch, when the sports participant applies pressure to the heel of the shoe, thereby encouraging the sports participant to maintain weight on the forward part of the foot. The alarm may be an audible alarm and may be removably attached to an upper portion of the shoe, prior to triggering. In one aspect, triggering the alarm comprises causing the alarm to emit an audible sound. The switch and the alarm may be enclosed in a casing, and removably attaching the switch may comprise removably attaching the casing to the shoe. The casing may additionally comprise a clip at either end, and removably attaching the casing to the shoe may comprise clipping the casing to the shoe at points below an inner and an outer ankle of the sports participant. The sports participant may be a tennis player, and removably attaching the switch may comprise removably attaching the switch to at least one sole of the tennis player's shoe.

In yet another aspect, a sports footwork training device according to the present invention comprises a switch removably attachable to a rearward portion of a lower surface of a sole of a shoe, the switch closable by application of pressure to a heel of a shoe, and means coupled to the switch for indicating closing of the switch. The means for indicating may comprise an audible alarm.

BRIEF DESCRIPTION OF THE DRAWINGS

The subject matter which is regarded as the invention is particularly pointed out and distinctly claimed in the concluding portion of the specification. The invention, however, both as to organization and method of practice, together with further objects and advantages thereof, may best be understood by reference to the following detailed description of the preferred embodiment(s) and the accompanying drawings in which:

DETAILED DESCRIPTION OF PREFERRED EMBODIMENTS

Figure 1:
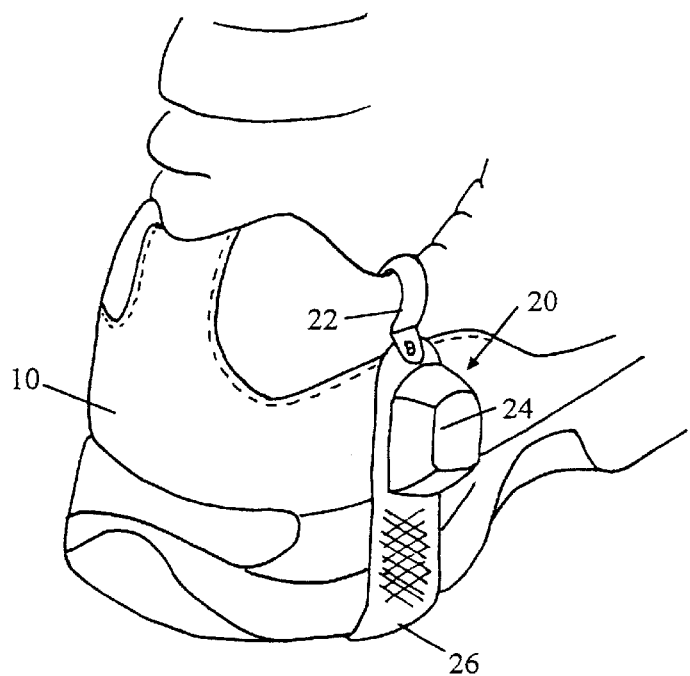
FIG. 1 is a side perspective view of a sports footwork training device constructed in accordance with one embodiment of the present invention shown removably attached to a shoe.
Figure 2:
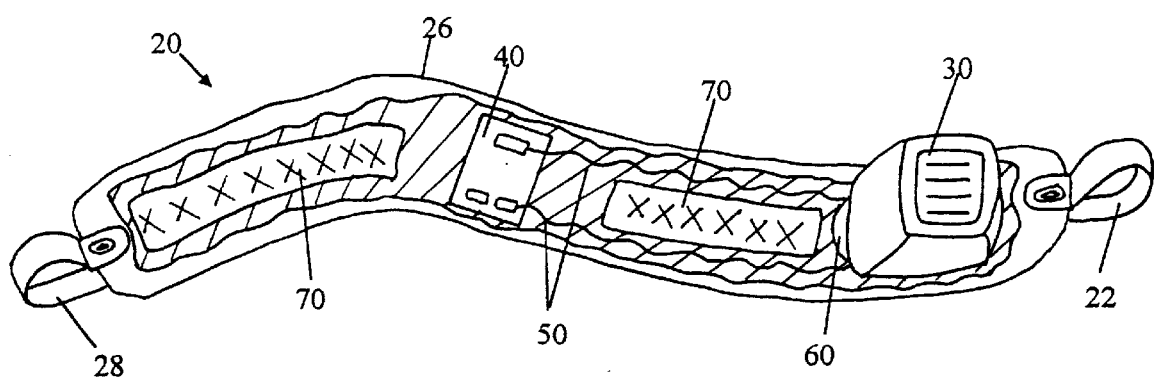
FIG. 2 is a cut-away top view of the tennis training device of the present invention showing an elasticized casing enclosing a switch connected to an audible alarm, and a battery holder, with clips for attachment to a shoe.

Referring to FIGS. 1 and 2, a preferred embodiment of the present invention is illustrated. FIG. 1 shows a tennis shoe 10 having attached thereto A sports footwork training device 20 according to the present invention. Device 20 is fastened to shoe 10 by attaching clip 22, which is adjacent to alarm pocket 24, to shoe 10 at a position below an outer ankle. Casing 26, which is elasticized, is stretched under the rearward or heel part of shoe 10 and clipped to shoe 10 by clip 28 (see FIG. 2) at a position below the opposite ankle. FIG. 2 shows a cut-away perspective view of tennis training device 20. Tennis training device 20 includes audible alarm 30, contained within alarm pocket 24 and disposed on the outer side of shoe 10, and switch 40, which is to be positioned beneath the heel of shoe 10 during use.

In operation during a tennis training session, switch 40 is open when the player's weight is on the toe or forward part of the foot or shoe, and is closed by the pressure produced when the player's weight is fully or partially applied to the heel of the shoe. Alarm 30 sounds when switch 40 is closed. Alarm 30 continues to sound until the player corrects his/her position and achieves the proper stance by redistributing his/her weight to the forward part of the foot. Through the use of a tennis training device according to the present invention, players can be trained to maintain their weight on the balls of their feet, and thereby improve their play at the net. A single training device may be used to monitor whether a player's weight is being maintained on the forward part of one foot, or two devices may be used, one to monitor each foot. If desired, tennis training device 20 may be alternately configured so that alarm 30 sounds when switch 40 is open. Using this configuration, players will hear a continuous tone when holding their weight on the balls of the feet, reinforcing that they are standing and moving properly, and will hear no sound from alarm 30, when exerting pressure on switch 40 by maintaining at least a part of their weight on the heel to which switch 40 is attached, the lack of sound indicating that they are not holding the desired stance.

Casing 26 encloses switch 40 and its associated electrical wiring or leads 50. Switch 40 is electrically connected to alarm 30 through electrical leads 50. In the embodiment illustrated in FIG. 1, alarm 30 is shown as enclosed by casing 26, but it may be alternately attached to the outside of casing 26. Alarm 30 is situated at an end of casing 26, so it will be positioned above the sole of shoe 10 when tennis training device 20 is attached to shoe 10. Typically, device 20 is worn with alarm 30 facing out, so as to minimize contact of the opposite foot and leg with alarm 30.

Alarm 30 is typically a buzzer, such as a standard 400 kHz, 3 volt buzzer. Such buzzers are commercially available. For example, one suitable alarm is a Model No. 20F1030L buzzer, manufactured by Kayer Industrial Co., Ltd., Hong Kong. Similar buzzers may be obtained from Radio Shack. Other types of sound generating devices are readily available, and may be used. Alarm 30 may be alternately a visual alarm, such as an electric light, or an electronic device, including a light-emitting diode. Alarm 30 may be alternately a vibrational alarm, such as the vibrating alarms commonly employed in pagers. Alarm 30 is powered by a battery (see FIG. 5), for example, a standard 20 mm, 3 volt coin cell lithium battery. The battery is contained within battery housing 60, such as a low profile surface mount battery holder, which is attached directly to alarm 30.

In another embodiment, the alarm may be housed in a casing or other type of compartment separate from the switch. The alarm may be coupled to the switch electrically, or a wireless alarm circuit, known in the art, can be incorporated in the device. A remote alarm may be energized when a signal is transmitted indicating that the switch is closed, or, as described above, the device may be alternately configured so that the alarm is energized when the switch is closed.

An enable/disable, or on/off, switch may also be provided for the tennis training device of the present invention. The function of such a switch is to prevent or allow triggering of the alarm, as desired. For example, a player may wish to disable the alarm while preparing for a training session, or after completion of the session, and to enable the alarm during the session. The enable/disable switch may be connected at any convenient location in the electrical circuit that includes switch 40 and alarm 30. Alternately, the device may be functionally disabled by rotating switch 40 to the back of shoe 10, so the player's weight may not be applied to switch 40. In order to perform the rotation conveniently, it may be advantageous to use a flexible material for casing 26.

Casing 26 is preferably constructed of a durable, abrasion-resistant fabric such as nylon and elasticized using elastic strips 70. Materials other than fabric may be used, for example, plastic films or durable nonwovens such as felt. The function of elastic strips 70 is to enable tennis training device 20 to fit snugly around shoes of varying sizes so that device 20 does not come off easily during use. Other means of performing this function are encompassed, including, for example, fabricating casing 26 from an elastic material such as an elasticized fabric. Elastic strips 70 may be attached at positions other than those shown, or supplemented or replaced by other means of fitting device 20 to a shoe snugly as described above. It may also be desirable to cover the outside of the section of casing 26 that covers the heel with a non-skid, non-marking material to provide improved traction for the player and to protect the court surface, or to construct casing 26 of such a material.

Tennis training device 20 is attached to shoe 10 by clips 22 and 28, below each ankle. Other means of attaching tennis training device 20 to shoe 10 securely and removably may be used, including fasteners which are well known in the prior art, such as snaps, straps, Velcro® fasteners, or fasteners similar to the Velcro® type, for example.

Figure 3:
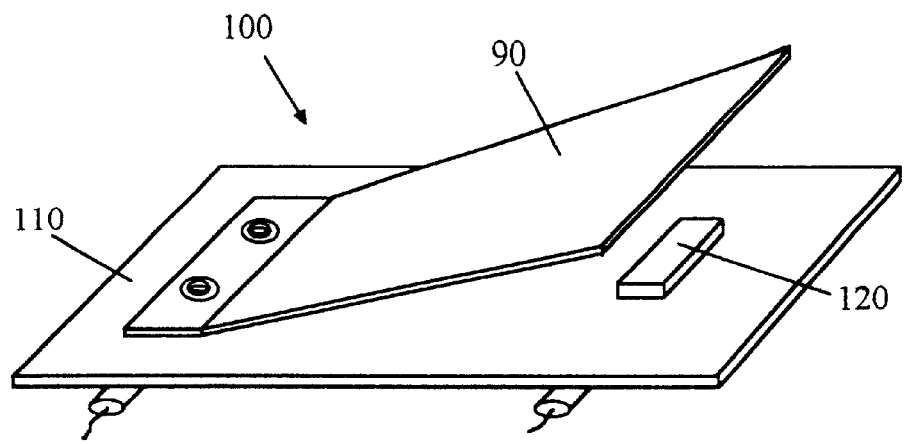
FIG. 3 is a perspective view of an exemplary switch used in the embodiment of the present invention shown in FIGS. 1 and 2.
Figure 4:
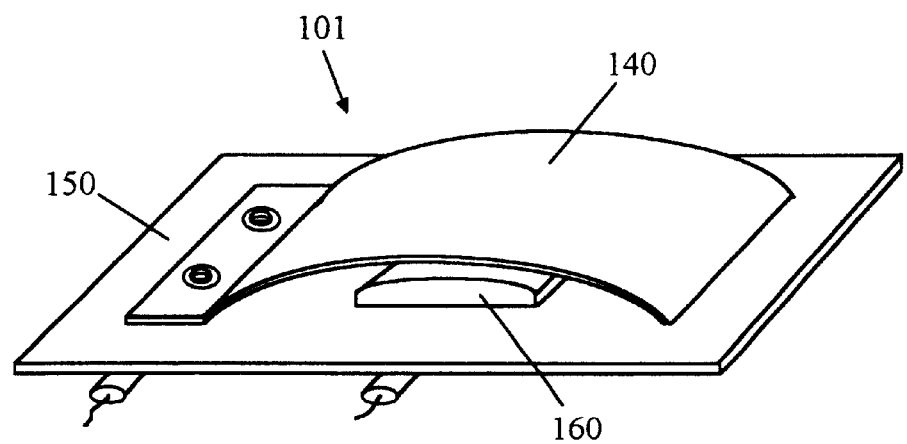
FIG. 4 is a side elevation view of an alternate type of switch useful in A sports footwork training device according to the present invention.

FIG. 3 shows one embodiment of a switch that can be used as part of the tennis training device of the present invention, switch 100. In this embodiment, a thin sheet 90 of electrically conducting elastic material, for example, 0.010 inch (0.25 mm) spring steel, is attached at one end to a slightly larger base 110 made of a strong, non-conducting material, for example, 0.062 inch (1.6 mm) phenolic plastic. The portion of the conducting elastic material not affixed to base 110 so that the end of the bent end is about 4 mm from the base. A knob 120 of conducting material, for example, a metal rivet, is attached to base 110 below the raised end of sheet 90. When sufficient pressure from the tennis player's weight on the heel is applied to the raised end of sheet 90, it will touch knob 120 below it, and switch 20 will be in the closed position. When the pressure is released, sheet 90 will return to its raised position, and switch 20 will be in the open position. Electrical connections are made to sheet 90 at the point where it attaches to base 110 and to knob 120 at the point where it attaches to base 110. FIG. 4 shows another embodiment of a switch that may be used. Switch 101 is constructed of flexible conducting sheet 140 attached to non-conducting base plate 150 in at least two points so as to form an arch above conducting knob 160. The materials described above as suitable for switch 100 are similarly suitable for switch 101. Electrical connections are made to sheet 140 at a point where it attaches to base plate 150 and to knob 160. Switch 101 operates similarly to switch 100; the pressure resulting from a tennis player's weight on his/her heel causes sheet 140 to touch knob 160, closing the circuit, and sounding an alarm connected thereto. When the pressure is released, sheet 140 returns to its original position, the circuit is opened, and the alarm is silent.

Many types of switches are designed to respond to changes in pressure. Any of these may be used as a switch in accordance with the present invention if the switch is sized to fit under an elevated heel of a shoe, and is sufficiently durable to withstand being stepped on repeatedly without failing. A pressure switch such as is known in the art may be used. One type of pressure switch is formed of two pieces of flexible metal laid on top of one another, and electrically insulated from one another until pressure is applied. Such switches are commonly used in the manufacture of pressure pads used in alarm systems. For example, Controlflex® Ribbon Switches from Tapeswitch Corporation, Farmingdale, N. Y., may be used. Another type of switch uses a piezoelectric material having conductive properties that change with pressure. While other types of switches that can respond to changes in pressure applied thereto are possible, those discussed above are exemplary of ones that can be used to achieve the desired result.

Figure 5:
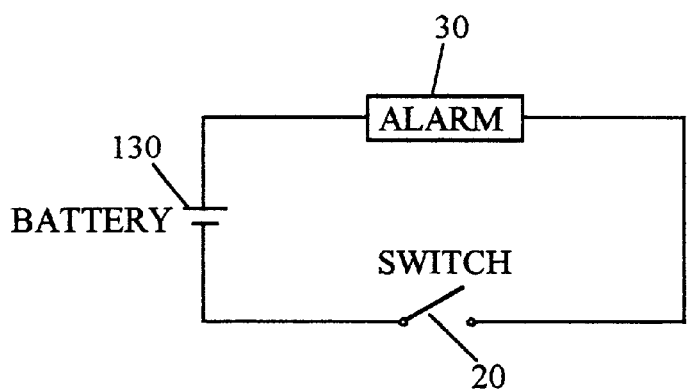
FIG. 5 is a block diagram of a sound-generating circuit used in the embodiment of the tennis training device of the present invention shown in FIGS. 1 and 2.

FIG. 5 shows a circuit diagram of the electrical connections of the present invention. Switch 20 and alarm 30 are electrically connected in series with battery 130, which powers alarm 30.

While the invention has been particularly shown and described with reference to preferred embodiment(s) thereof, it will be understood by those skilled in the art that various changes in form and details may be made therein without departing from the spirit and scope of the invention.

What is claimed is:

1. A sports footwork training device for use with a shoe worn by a user comprising:
    a switch adapted to be in a closed position while body weight of the user is being applied to a heel of the shoe;
    an alarm, electrically coupled to the switch;
    a casing enclosing the switch, the casing adapted to fasten the switch to a rearward portion of an outside surface of a sole of a shoe; and
    means for affixing the casing to the shoe, secured to the casing;
    whereby the alarm is triggered while body weight of the user is being applied to the heel of the shoe.

2. A sports footwork training device according to claim 1, wherein said alarm comprises an audible alarm.

3. A sports footwork training device according to claim 1, wherein said alarm and said means for operating said alarm are enclosed in a casing.

4. A sports footwork training device according to claim 3, wherein said casing is flexible.

5. A sports footwork training device according to claim 3, wherein said casing additionally comprises a battery holder.

6. A sports footwork training device according to claim 3, wherein said casing is expandable.

7. A sports footwork training device according to claim 1, additionally comprising at least one clip for removably attaching said means for operating said alarm to the shoe.

8. A sports footwork training device according to claim 1, wherein said alarm is removably attachable to the shoe.

9. A sports footwork training device according to claim 8, additionally comprising at least one clip for removably attaching said alarm to the shoe.

10. A sports footwork training device for use with a shoe worn by a user comprising:
    a switch adapted to be in a open position while body weight of the user is being applied to a heel of the shoe;
    an alarm, electrically coupled to the switch;
    a casing enclosing the switch, the casing adapted to fasten the switch to a rearward portion of an outside surface of a sole of a shoe; and
    means for affixing the casing to the shoe, secured to the casing; whereby the alarm is triggered while body weight of the user is being applied to the heel of the shoe.

11. A sports footwork training device according to claim 10, wherein said alarm is removably attachable to the shoe.

12. A method for training a sports participant to maintain weight on a forward part of a foot, said method comprising:
    removably attaching, to a rearward portion of a lower surface of at least one sole of the sports participant's shoe, a switch closable by application of pressure to a heel of the shoe; and
    triggering an alarm, electrically coupled to said switch, when the sports participant applies pressure to the heel of the shoe, thereby encouraging the sports participant to maintain weight on the forward part of the foot.

13. The method of claim 12, additionally comprising, prior to triggering said alarm, removably attaching said alarm to an upper portion of the shoe.

14. The method of claim 12, wherein said alarm comprises an audible alarm, and wherein triggering said alarm comprises causing said alarm to emit an audible sound.

15. The method of claim 12, wherein said switch and said alarm are enclosed in a casing, and wherein removably attaching said switch comprises removably attaching said casing to the shoe.

16. The method of claim 15, wherein said casing additionally comprises a clip at either end, and wherein removably attaching said casing to the shoe comprises clipping said casing to the shoe at points below an inner and an outer ankle of the sports participant.

17. The method of claim 12, wherein said sports participant is a tennis player, and wherein removably attaching said switch comprises removably attaching said switch to at least one sole of the tennis player's shoe.

* * * * *